United States Patent

Christian et al.

[11] Patent Number: 6,152,902
[45] Date of Patent: Nov. 28, 2000

[54] METHOD AND APPARATUS FOR COLLECTING SURGICAL FLUIDS

[75] Inventors: Jeffrey J. Christian, San Jose; David Curtis Dillow, Cupertino, both of Calif.

[73] Assignee: Ethicon, Inc., Somerville, N.J.

[21] Appl. No.: 08/868,429

[22] Filed: Jun. 3, 1997

[51] Int. Cl.[7] .................................................. A61M 1/00
[52] U.S. Cl. ............................................ 604/320; 604/319
[58] Field of Search .................................. 604/317, 319, 604/320, 323; 128/760

[56] References Cited

U.S. PATENT DOCUMENTS

| | | |
|---|---|---|
| 3,699,815 | 10/1972 | Holbrook . |
| 3,704,709 | 12/1972 | Sorenson et al. . |
| 3,745,999 | 7/1973 | Deaton . |
| 3,845,765 | 11/1974 | Ikeda . |
| 4,060,107 | 11/1977 | Naftulin . |
| 4,321,922 | 3/1982 | Deaton . |
| 4,346,711 | 8/1982 | Agdanowski et al. . |
| 4,384,580 | 5/1983 | Leviton ................................ 604/119 |
| 4,388,922 | 6/1983 | Telang ................................ 604/319 |
| 4,402,687 | 9/1983 | Denty et al. ........................ 604/319 |
| 4,419,093 | 12/1983 | Deaton . |
| 4,460,391 | 7/1984 | Nichols ............................... 604/319 |
| 4,516,973 | 5/1985 | Telang . |
| 4,522,623 | 6/1985 | Lauterjung . |
| 4,675,010 | 6/1987 | Siposs et al. . |
| 4,675,011 | 6/1987 | Kurtz et al. ........................ 604/320 |
| 4,775,360 | 10/1988 | Lane et al. . |
| 4,795,448 | 1/1989 | Stacey et al. . |
| 4,798,578 | 1/1989 | Ranford . |
| 4,898,593 | 2/1990 | Swisher et al. .................... 604/319 |
| 4,930,997 | 6/1990 | Bennett . |
| 5,112,323 | 5/1992 | Winkler et al. . |
| 5,158,533 | 10/1992 | Strauss et al. ..................... 604/319 |
| 5,185,007 | 2/1993 | Middaugh et al. . |
| 5,234,419 | 8/1993 | Bryant et al. . |
| 5,279,602 | 1/1994 | Middaugh et al. . |
| 5,437,836 | 8/1995 | Yamada . |
| 5,470,324 | 11/1995 | Cook et al. . |
| 5,725,516 | 3/1998 | Cook et al. ........................ 604/319 |

Primary Examiner—John G. Weiss
Assistant Examiner—David J. Cho
Attorney, Agent, or Firm—Verne E. Kreger, Jr.

[57] ABSTRACT

Surgical fluid collection devices, systems and methods allow individual containers to be coupled in series using a single inflow port and a single outflow port on each container. Surgical fluids are sealed within a disposable liner in each container. In most embodiments, a one-way valve of the liner seals surgical fluid within the liner to prevent spillage to a surrounding vacuum chamber, and allows flow from the surrounding vacuum chamber into the interior of the liner to equalize pressure across the liner. This arrangement allows the use of flexible, inexpensive liners with large interior volumes, without having to resort to complex pressure equalizing arrangements. A sterilizable polymer receptacle is also provided which can withstand the large pressure forces associated with large fluid collection volumes.

14 Claims, 3 Drawing Sheets

METHOD AND APPARATUS FOR COLLECTING SURGICAL FLUIDS

BACKGROUND OF THE INVENTION

1. Field of the Invention

The present invention generally relates to medical procedures and devices, and in particular, provides devices, systems, and methods for collecting surgical fluids during minimally invasive electrosurgery and other procedures.

Electrocautery has been in use for many years as a general surgical tool, particularly for procedures such as transcervical fibroid removal. In a typical fibroid removal, the uterus is flooded under sufficient fluid pressure to separate the walls of the uterus and render the surgical site suitable for observation. This procedure is generally described as uterine cavity distension. During flooding, an electrocautery surgical tool is positioned within the uterus through the cervix. Electrical current at high voltage settings is transmitted from a cutting surface of the surgical instrument to the surgical site. The electrosurgical device may be either monopolar or bipolar, and the distension fluid may be nonconductive or conductive.

The electrical current is concentrated at the cutting surface. Heat generated from the resistance of tissue to the flow of electrical current is high enough to vaporize cells near the cutting surface. Thus, a cut is made with little physical resistance to the cutting motion, and heat from the cut cauterizes small blood vessels, helping to maintain visibility and control.

Traditionally, electrosurgical resection of large quantities of tissue has required intermediate flushing of the internal surgical site to remove the severed tissue and electrosurgical debris. While such intermittent flushing can restore image quality, it greatly lengthens the time required for complete removal of the targeted endometrial tissues during fibroid removal.

More recently, continuous tissue removal methods and devices have been developed which greatly increase the speed of electrosurgical resection. In particular, resectors have been developed which include morcellators to fragment and remove the severed tissues during resection. Additionally, brute electrosurgical vaporization is now used to remove tissues, while a continuous flow of fluid over the surgical site from the direction of the viewing scope maintains image quality. Each of these new, improved procedures involves a significant increase in total fluid volume, as compared to the intermittent flushing of traditional electrosurgery.

A variety of additional surgical procedures have also been developed using large volumes of fluid, together with laser vaporization, microwave heating (often using a cooled fluid), heated and/or cooled fluids for direct tissue ablation, and the like. Hence, a wide variety of therapies, both minimally invasive and traditional, now make use of large volumes of surgical fluids. The collection and disposal of these large volumes of surgical fluid have become increasingly problematic.

A variety of fluid collection devices are currently available. Unfortunately, existing surgical fluid collection systems were often designed with a small container size, as this was generally sufficient for intermittent flushing. In light of the increasing awareness of the dangers posed by blood and other surgical debris, these known small devices have been modified to include disposable liners.

Known lined collection systems have two primary disadvantages. First, a vacuum within the container often draws the fluids into the liner from the surgical site, and known container structures would often collapse under the pressure load if they were resized for modern fluid volumes. In other words, simply increasing the size of existing liners to accommodate increased quantities of surgical fluid can result in large pressure loads across the liner and/or the surrounding vacuum chamber structure, requiring unwieldy and expensive structures.

The second major disadvantage of existing surgical fluid collection systems is that a complex arrangement of tubing is often required to accommodate the numerous small containers and disposable liners. This complexity increases the set-up and break-down time, increases the likelihood of an error during set-up, and greatly increases the probability that contaminated surgical fluids will spill during detachment and removal of the liners.

In light of the above, it would be desirable to provide improved surgical fluid collection devices and methods. It would be particularly advantageous if such improved devices and methods could accommodate the large volumes of surgical fluids which are a by-product of many of the new minimally invasive surgical procedures. It would be especially desirable if such improved devices and methods included a simplified connection arrangement, and facilitated the safe disposal of surgical fluids with minimum risk to the attending medical personnel.

2. Description of the Background Art

U.S. Pat. No. 4,516,973 describes a one piece disposable collection bag having a rigid cover. U.S. Pat. No. 4,675,010 describes a thoracic drainage collection system and method which makes use of a flexible disposable collection bag. U.S. Pat. No. 5,470,324 describes a non-refluxing suction canister system.

U.S. Pat. No. 5,279,602 describes a suction drainage infection control system, while U.S. Pat. No. 5,437,836 describes a method of, and container for, treating waste liquid containing body fluid. U.S. Pat. Nos. 5,234,419 and 5,185,007 describes suction drainage infection control systems.

U.S. Pat. Nos. 4,419,093, 4,321,922 and 3,745,999 describe methods of receiving and disposing of fluids from the body, and related devices. U.S. Pat. No. 5,112,323 describes a wound evacuator. U.S. Pat. Nos. 4,930,997, 4,798,578, 4,795,448, 4,775,360, 4,522,623, 4,346,711, 4,060,107, 3,845,765, 3,704,709, and 3,699,815 are also relevant.

SUMMARY OF THE INVENTION

The present invention provides surgical fluid collection devices, systems, and methods which are particularly well suited for collection of large volumes of surgical fluids. A simplified collection system allows individual containers to be coupled in series using a single inflow port and a single outflow port on each container. The containers typically include a disposable liner within a vacuum chamber of a rigid receptacle. A one-way valve of the liner prevents the fluid from spilling to the surrounding vacuum chamber, and also admits air from the surrounding vacuum chamber into the interior of the liner to equalize pressure across the liner when a vacuum is drawn from within the liner. This arrangement allows the use of inexpensive liners with large interior volumes, without having to resort to complex tubing arrangements to equalize pressure. A sterilizable polymer receptacle is also provided which can withstand the large pressure forces associated with large fluid collection volumes.

In a first aspect, the present invention provides a surgical fluid collector comprising at least one container. Each container includes a receptacle having a rigid receptacle body and a lid. The receptacle body has an open end, over which the lid is sealable to define a vacuum chamber. A liner is disposable within the vacuum chamber of the receptacle, and defines a liner interior. Vacuum and fluid inflow ports are in fluid connection with the interior of the liner through the rigid receptacle. A valve is disposed between the interior of the liner and the vacuum chamber surrounding the liner. The valve allows flow into the interior of the liner, but prevents surgical fluid from flowing from the interior of the liner to the surrounding vacuum chamber. The valve thereby equalizes pressure across the liner material when a vacuum is drawn through the vacuum port, the valve typically comprising a simple, low cost, and reliable one-way valve.

In another aspect, the present invention provides a surgical fluid collection system comprising a plurality of containers. Each container comprises a receptacle which defines a vacuum chamber. A liner is disposable within the vacuum chamber of the receptacle, and defines a liner interior. Vacuum and fluid inflow ports are in fluid communication with the interior of the liner through the receptacle. A surgical fluid inflow tube is coupleable to the inflow valve of a first container to drain surgical fluids from a patient body. An intercontainer tube couples the fluid port of a second container with the vacuum port of the first container. Hence, the surgical fluids flow through the liner of the first container and into the liner of the second container when the liner of the first container is full. In most embodiments, each liner holds at least five liters of surgical fluid, and the liners have a combined capacity of at least 20 liters of surgical fluid.

In another aspect, the present invention provides a rigid receptacle for use with a disposable surgical fluid collector liner. The liner defines a liner interior, and has a valve which allows flow into the interior of the liner, but which prevents surgical fluid from flowing out from the interior of the liner. The receptacle comprises a rigid polymer body having an open end. A lid is sealable over the open end of the body to define a vacuum chamber. The vacuum chamber has a volume of at least five liters. First and second passages extend through either the lid or the body to provide fluid communication to the interior of the liner.

In yet another aspect, the present invention provides a disposable surgical fluid collector liner for use with a rigid receptacle. The receptacle defines a vacuum chamber, and has first and second passages into the vacuum chamber. The liner comprises a flexible pouch bordering an interior of the liner. A vacuum port is in fluid communication with the interior of the liner through the first passage of the receptacle, while a fluid inflow port is similarly in fluid communication with the interior of the liner through the second passage. A valve is disposable between the interior of the liner and the vacuum chamber surrounding the liner. The valve allows flow into the interior of the liner, but prevents surgical fluid from flowing from within the liner to the surrounding vacuum chamber.

In a method according to the present invention, a vacuum is drawn within a flexible liner while the liner is disposed within a rigid vacuum chamber by coupling a vacuum source to an interior of the liner. The vacuum is distributed within the vacuum chamber surrounding the liner by a one-way valve. Surgical fluids are aspirated from a patient body and into the liner with the vacuum, and the one-way valve prevents the surgical fluids from spilling out of the liner to the surrounding vacuum chamber.

DETAILED DESCRIPTION OF THE SPECIFIC EMBODIMENTS

The present invention allows the collection of surgical fluids into large fluid reservoirs which are connected in a simple series arrangement. This simplified arrangement facilitates the setting-up and breaking-down of the fluid collection system, and also enhances the ease and safety of transporting and disposing of the collected surgical fluids. Hence, the present invention will find applications in a wide variety of medical procedures, including both minimally invasive and open surgical therapies, postoperative care, and the like. The surgical fluid containers, systems, and methods of the present invention will find their most immediate application in minimally invasive surgeries of the thorax, pelvic region, and joints, particularly when such minimally invasive surgeries are performed at an internal surgical site flooded with saline, sorbitol, mannitol, sorbitol-mannitol, or any other conductive or nonconductive fluid medium. The present invention is particularly well suited for use in resection and/or ablation of the endometrial lining of the uterus.

Figure 1:
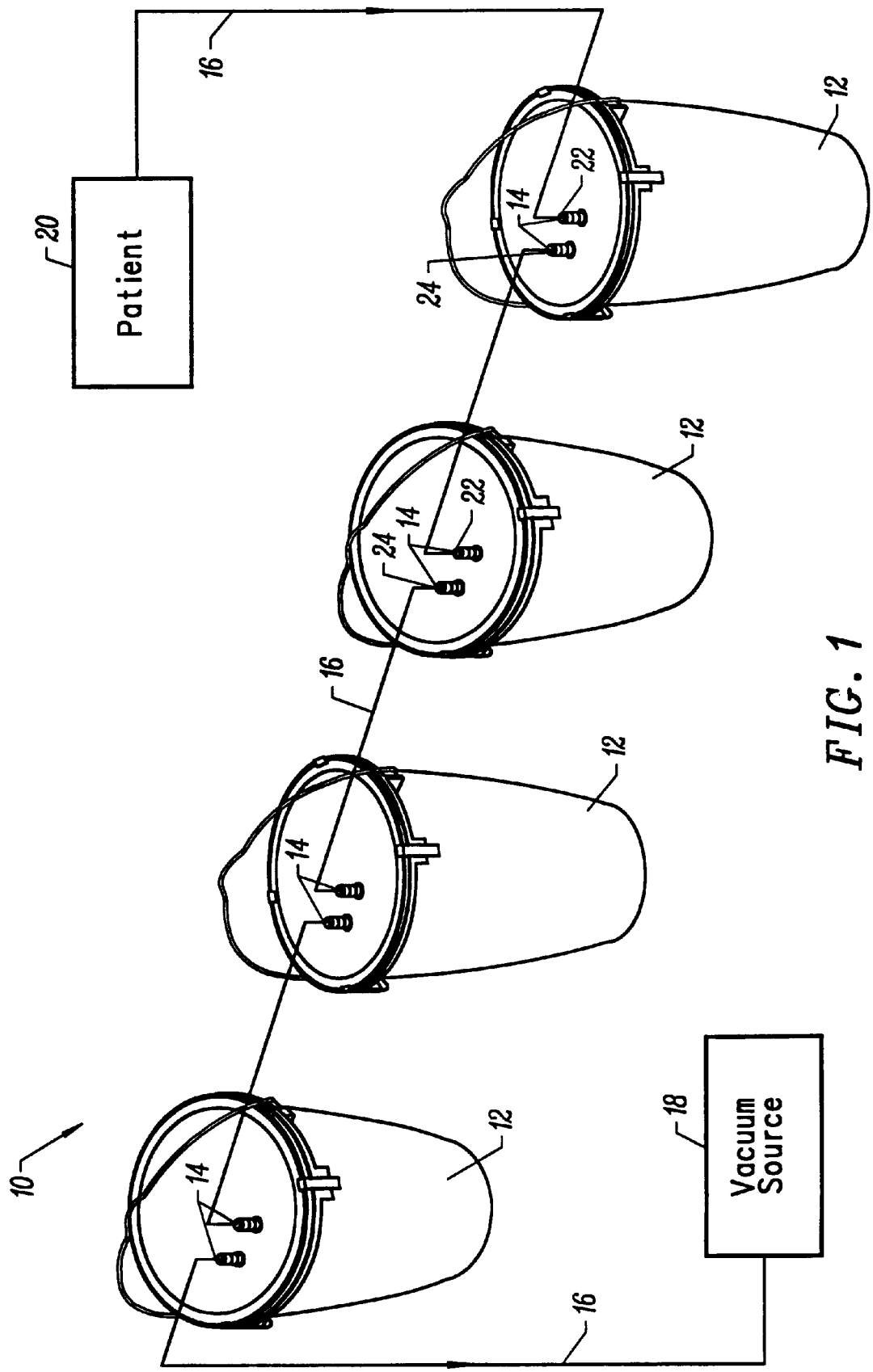
FIG. 1 illustrates a system and method for collecting surgical fluids according to the principles of the present invention.

Referring now to FIG. 1, a surgical fluid collection system 10 includes four surgical fluid containers 12 coupled together in series. Each container 12 has a pair of ports 14. Tubing 16 couples containers 12 each other, to a vacuum source 18, and to a source of surgical fluids from a patient 20. For example, tubing 16 may couple containers 12 to an endometrial resection probe such as that described in copending U.S. patent application Ser. No. 08/542,289, filed Oct. 12, 1995 (Attorney Docket No. 16944-000130), the disclosure of which in incorporated herein by reference.

The combined volume of containers 12 will generally have a capacity of at least about 10 liters, preferably being more than about 20 liters to accommodate the large amounts of surgical fluids used in some of the recently developed minimally invasive surgical procedures. To accommodate such large quantities of fluid, each container 12 will preferably have a capacity of greater than about 5 liters, ideally having a capacity of about 8 liters. This gives fluid collection system 10 a total capacity of about 32 liters with four containers. This total fluid capacity can easily be varied by coupling additional containers 12 in system 10. Generally, between three and seven containers will be included to avoid the complexity of larger numbers of containers and intercontainer connector tubes, and also to limit the weight of each full container for ease of handling and disposal.

In each of containers 12, one of ports 14 acts as a fluid inflow port 22, through which the surgical fluid from patient 20 enters the container. Similarly, the other port 14 acts as a vacuum port 24 through which vacuum source 18 draws down the internal pressure within the container. Once the container has reached its predetermined capacity, surgical fluids which enter inflow port 22 will pass through container 12 and out vacuum port 24 for storage within another of the containers.

The use of a single port for application of a vacuum, and also for transferring overflow surgical fluids to an adjacent container, allows the operation of surgical fluid collection system 10 with only two ports per container. This simple serial or "daisy-chain" connection allows the surgical staff to vary the capacity of fluid collection system 10 by simply increasing or decreasing the number of containers 12 which are connected in line between patient 20 and vacuum source 18. Additionally, the lack of any branching interconnections along tubing 16 minimizes residue and simplifies postoperative cleanup. Allowing air to enter the system after the fluid has been collected may help to clear any residual surgical fluids from the tubing and distribute it entirely within containers 12, thereby minimizing the likelihood of any significant spillage while separating the elements of collection system 10.

Figure 2:
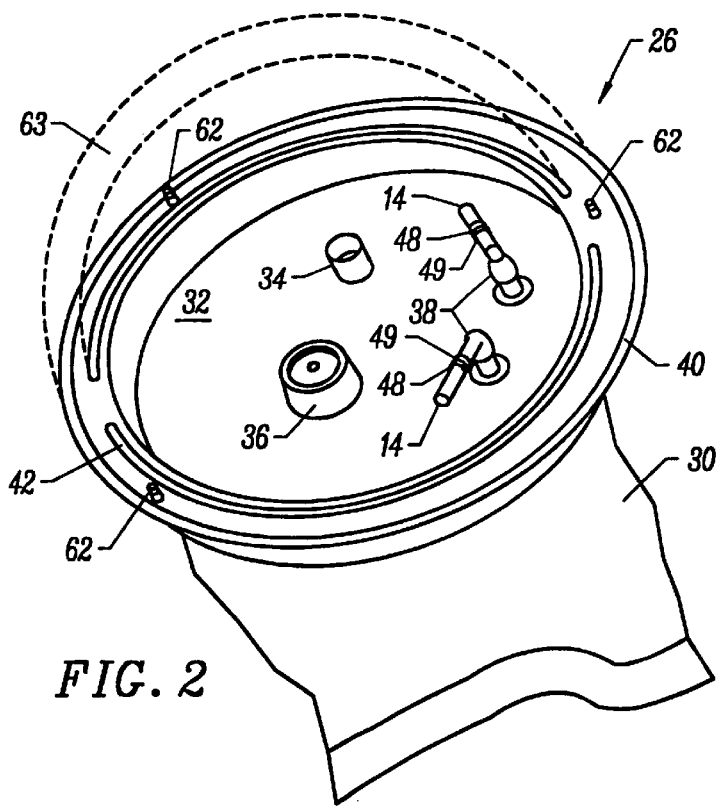
FIG. 2 illustrates a disposable surgical fluid container liner, for use in the system of FIG. 1.
Figure 3:
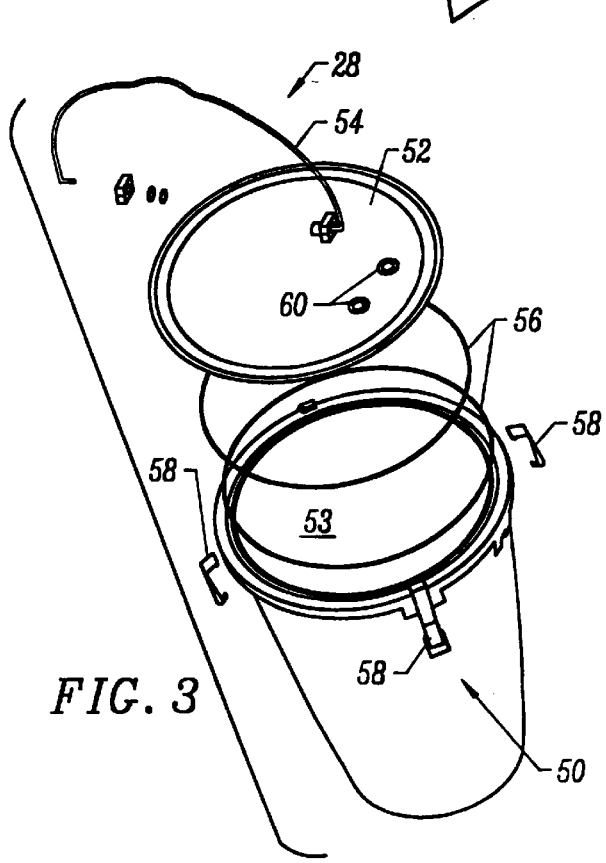
FIG. 3 is an exploded view of a rigid polymer receptacle for use in the system of FIG. 1.
Figure 4:
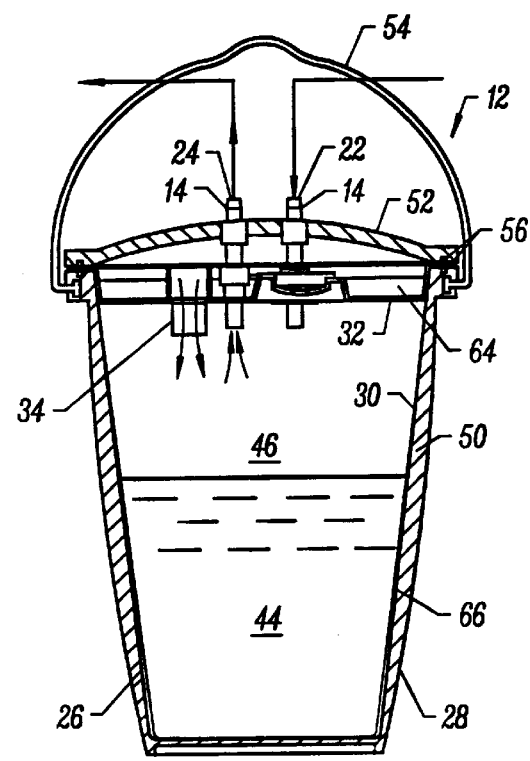
FIG. 4 is a cross-sectional view of a surgical fluid container in which the liner of FIG. 2 is removably disposed within the rigid receptacle of FIG. 3, as used in the system of FIG. 1.

Referring now to FIGS. 2–4, each container 12 generally comprises a disposable liner 26 and a rigid receptacle 28. Liner 26 includes a flexible polymeric pouch 30 which is sealed about the lower perimeter of a semi-rigid or rigid lid 32. Lid 32 supports a one-way valve 34, a sealable cap 36, and a pair of knock-down valves 38. A rim 40 extends radially from lid 32, and a significant portion of the rim is separated from the lid by a circumferential slot 42.

Surgical fluids 44 (see FIG. 4) are contained within an interior 46 of liner 26. Liner interior 46 is sealed by the surrounding flexible pouch 30 and lid 32, with the exception of break-down valves 38, cap 36, and one-way valve 34. Flexible pouch 30 typically comprises a polymer such as polyvinyl chloride (PVC), but may be formed of a wide variety of alternative materials. Similarly, lid 32 ideally comprises acrylic butadiene styrene (ABS), but may alternatively be formed from a variety of materials. Lid 32 will generally have sufficient strength to substantially maintain its shape while supporting the weight of surgical fluid 44, so as to facilitate removal of disposable liner 26 from receptacle 28.

One-way valve 34 is arranged to allow flow from outside liner 26 to the liner interior 46, but to block flow from the interior of the liner to the surrounding environment. Thus, one-way valve 34 prevents the release of surgical fluids from liner interior 46 once the liner is full. One-way valve 34 preferably comprises a simple diaphragm flapper valve such as that available commercially from Qosina of Edgewood, N.Y., under Model No. 51465. Sealable cap 36 allows access to the collected surgical fluid 44 for inspection and/or testing prior to disposal of the filled liner 26. Knock-down valves 38 are rotatably mounted to lid 32, and seal ports 14 from liner interior 46 when tubular bodies 48 are oriented horizontally. To open knock-down valves 38 and allow access through ports 14, tubular bodies 48 are simply oriented upward.

As can be understood most clearly with reference to FIGS. 3 and 4, rigid receptacle 28 generally comprises a receptacle body 50 and a receptacle lid 52. Receptacle body 50 and receptacle lid 52 define a vacuum chamber 53, and should ideally have sufficient strength and structural rigidity to withstand an external load of 1 atmosphere. To facilitate sterilization, minimize weight, and withstand the substantial pressure loads associated with the large volumes of surgical fluid of the new minimally invasive surgical procedures, receptacle body 50 and receptacle lid 52 are preferably formed of a high strength, high temperature polymer, such as Ultem® from General Electric. A handle 54 allows receptacle 28 to hang from an I.V. stand or the like. O-rings 56 are inset within grooves of the receptacle body 50 and receptacle lid 52, and the lid is clamped on to the body using clips 58. Alternatively, a gasket attached to liner rim 40 may allow sealing without O-rings.

Receptacle lid 52 includes two through holes 60 through which knockdown values 38 protrude when tubular bodies 48 are vertically oriented. Tubing bodies 48 have compliant rings 49 which seal against the lid material bordering holes 60. Protrusions 62 along rim 40 mate with detents in the receptacle lid to help align knock-down valves 38 with inserts 60.

Rim 40 of disposable liner 26 helps to seal receptacle 28, and also provides a handle which facilitates removal and disposal of the surgical fluids. Rim 40 is disposable between the O-rings 56 of receptacle lid 52 and receptacle body 50. As mentioned above, a gasket on rim 40 may provide sealing without O-rings. Once the disposable liner is full, the portion of rim 40 which is separated from lid 32 by slot 42 can be flexed upward away from the receptacle body. By flexing the two opposed portions of rim 40 upward and together, they define a convenient carrying handle 63 for removing and carrying the filled disposable pouch. As lid 32 substantially separates vacuum chamber 53 into an upper chamber 64 and a lower chamber 66, slots 42 also allow the pressure to equalize between these volumes, thereby avoiding the imposition of large pressure forces against the lid of the disposable liner.

In use, a member of the surgical team will determine the surgical fluid capacity required for a particular procedure, and will provide at least enough containers 12 to accommodate that predetermined fluid volume. A disposable liner 26 is placed in each receptacle body 50 with rim 40 engaging the associated O-ring 56. Optionally, protrusions on the bottom of rim 42 (similar to protrusions 62 on top of the rim) engage associated detents in the receptacle body (not shown). Tubular bodies 48 of knock-down valves 38 are oriented upward to open the valves, and to provide access to the interior of the liner through ports 14. Receptacle lid 52 is positioned over the receptacle body by sliding tubular bodies 48 through holes 60, and also by aligning protrusions 62 with associated detents in the bottom of the receptacle lid (not shown). O-ring 56 associated with receptacle lid 52 engages the top of rim 40 of disposable liner 26, so that the rim is sandwiched between the two O-rings. As tubular bodies 48 seal in holes 60, the only openings through receptacle 28 are ports 14, which are in communication with the interior of the liner.

As can be understood with reference to FIG. 1, tubing 16 couples a first of the containers with the source of surgical fluids within patient 20. This leaves only one open passage through the receptacle of the first container. In the exemplary embodiment, the two ports are identical, so that either port 14 can be used as fluid input port 22. The remaining port is then coupled to either of the two ports of an adjacent container 12, and through that container, on to the vacuum. As each container 12 has only two ports, and as they are interchangeable, there is little likelihood that fluid containment system 10 will be coupled together improperly.

The remaining containers are coupled to the vacuum ports of a preceding container until there are sufficient containers coupled together to accommodate the predetermined volume of surgical fluid. The final container is then coupled by tubing 16 to vacuum source 18. It should be understood that there may be valves, filters, pressure regulators, and the like disposed between containers 12 and vacuum source 18, and optionally between patient 20 and containers 12.

As can be understood with reference to FIGS. 1 and 4, vacuum source 18 draws down the pressure within each container 12 by withdrawing air and/or fluids through vacuum port 24. Pressure in interior 46 of liner 26 is equalized with the surrounding vacuum chamber 53 by air flowing through one-way valve 34 from around the liner, as shown in FIG. 4. Grooves or ridges within receptacle body 50 may help prevent flexible pouch 30 of liner 26 from sealing against the surrounding receptacle body, enhancing the distribution and equalization of pressure throughout the vacuum chamber (not shown). Air also flows from below lid 32 into upper chamber 64 through slots 42, which are shown most clearly in FIG. 2. Thus, pressure loads on both the flexible liner pouch and the liner lid are substantially avoided.

Fluid initially flows from patient 20 to the first container 12, where it is contained within the interior of the liner. As fluid 44 fills interior 46 of liner 26, one-way valve 34 equalizes pressure within liner interior 46 and surrounding the liner within vacuum chamber 53. However, once fluid 44 substantially fills liner interior 46, one-way valve 34 prevents the fluid from spilling out of the liner to the surrounding vacuum chamber. Additional fluid then begins to flow out through vacuum port 24.

Any additional fluid will then flow through the interior of the liner of the first container, and then on through tubing 16 to the inflow port 22 of the adjacent container 12. That adjacent container will then begin to fill, and if sufficient fluid is introduced from patient 20 to fill the second container, the overflow will again proceed on to the next container, and so on. The introduction of fluid will preferably cease before the final container is completely full.

Once fluid collection system 10 is full, or once the surgical procedure has ended, tubing 16 is detached from containers 12, and clips 58 are opened to allow receptacle lid 52 to be removed. Tubular bodies 48 of knock-down valves 38 are placed in a horizontal position, sealing fluid 44 within the interior 46 of liner 26.

By grasping rim 40 along slot 42, the rim can be flexed upward away from receptacle body 50. Thus, the rim forms a convenient handle for lifting the filled disposable liner 26 from the receptacle body, and for carrying surgical fluid 44 to a disposal site. One-way valve 34, sealable cap 36, and knock-down valves 38 prevent the leakage of surgical fluid 44, even if the liner is inadvertently dropped during transportation. Access to surgical fluid 44 may be provided by actuating one of the knock-down valves, or through sealable cap 36.

Figure 5A:
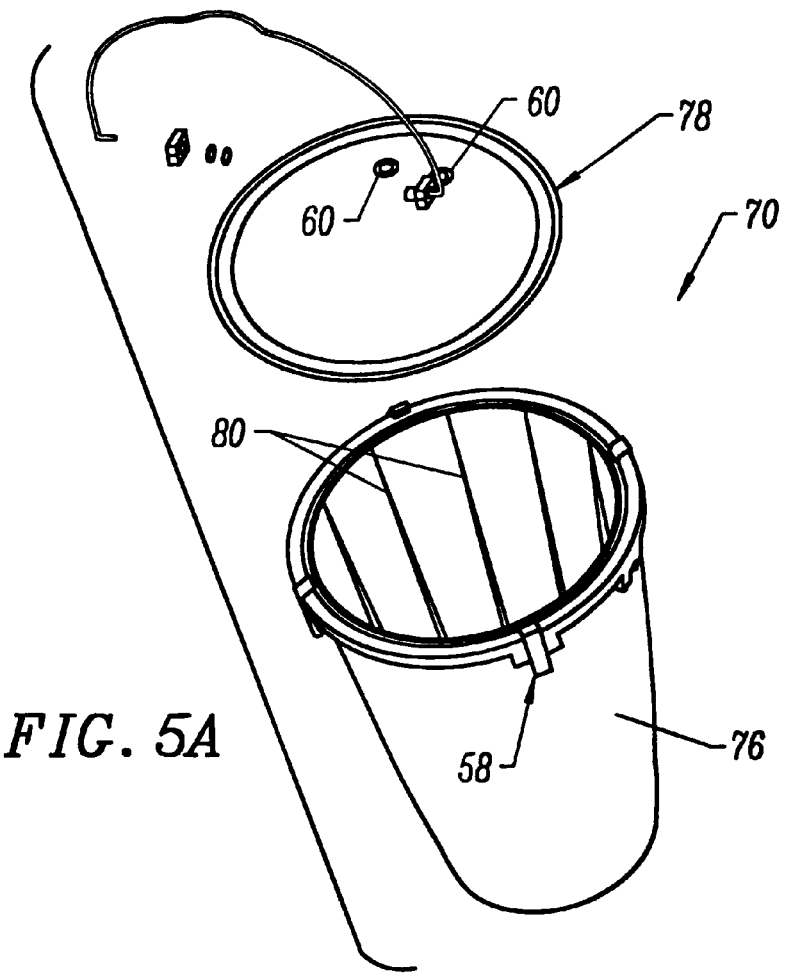
FIGS. 5A and 5B are perspective views of an alternative receptacle and liner, in which a gasket on the rim of the liner helps seal between the receptacle lid and body, and in which pinch valves on flexible tubing can seal the surgical fluid within the liner.
Figure 5B:
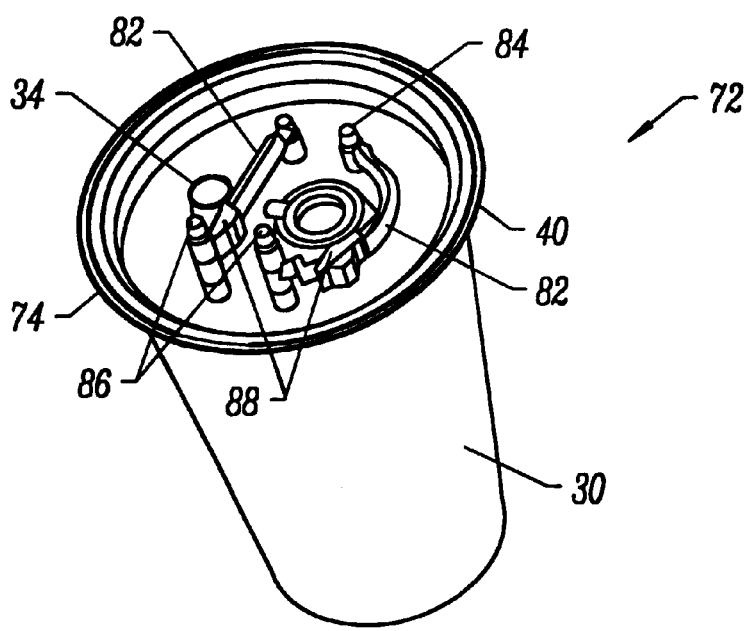

An alternative receptacle 70 and a corresponding liner 72 are illustrated in FIGS. 5A and 5B, respectively. Rim 40 is here provided with a gasket 74 to effect sealing between body 76 and lid 78. Gasket 74 extends onto the upper and lower surfaces of rim 40 to seal directly against the material of lid 78 and body 76, so that no O-rings are required. Ridges 80 reinforce body 76, and also distribute and equalize pressure around the liner.

Liner 72 includes flexible tubing 82 between angled fittings 84 and fixed tubular bodies 86. Pinch clamps 88 on tubing 82 seal the collected surgical fluids within the liner.

While the exemplary embodiments have been described in some detail, by way of example and for clarity of understanding, a variety of changes, modifications, and adaptations of the present invention will be obvious to those of skill in the art. For example, flexible tubes may couple the interior of the liner to fluid inflow and vacuum ports affixed to the receptacle. Thus, the scope of the present invention is limited solely by the appended claims.

What is claimed is:

1. A surgical fluid collector comprising at least a first and second container, the first container including:
   a receptacle having a rigid receptacle body and a lid, the receptacle body having an open end, the lid sealable over the open end to define a vacuum chamber;
   a liner disposable within the vacuum chamber of the receptacle, the liner defining a liner interior;
   a first port in fluid communication with the interior of the liner through the rigid receptacle and in fluid communication with a vacuum source and said second container and;
   a second port in fluid communication with the interior of the liner through the rigid receptacle and in fluid communication with the surgical fluid and;
   a valve disposed between the interior of the liner and the vacuum chamber surrounding the liner, the valve allowing flow into the interior of the liner and preventing surgical fluid from flowing from the interior of the liner to the surrounding vacuum chamber and;
   whereby when the first container is substantially full with surgical fluid, the surgical fluid flows via the first port to second container.

2. A collector as claimed in claim 1, wherein the valve comprises a one-way valve.

3. A collector as claimed in claim 1, wherein the liner comprises a flexible pouch and a lid which is more rigid than the liner pouch, and further comprising a rim extending radially from the liner lid, the rim being disposable between the receptacle body and the receptacle lid to help seal the vacuum chamber, the liner lid and rim substantially separating the vacuum chamber into an upper portion and a lower portion, an opening being disposed between the rim and the liner lid to equalize pressure between the upper portion and the lower portion of the vacuum chamber.

4. A collector as claimed in claim 3, wherein the opening comprises at least one slot which separates a portion of the rim from the adjacent liner lid, the portion of the rim defining a handle which is movable away from the liner lid to facilitate lifting the liner from the body of the receptacle.

5. A collector as claimed in claim 1, further comprising first and second tubular bodies which are extendable from the liner through the receptacle to the first port and the second port, respectively, the receptacle being sealed about the tubular bodies.

6. A collector as claimed in claim 5, further comprising a shut-off valve disposed along each tubular body to seal the interior of the liner.

7. A collector as claimed in claim 1, wherein the liner holds at least 5 liters of surgical fluid.

8. A collector as claimed in claim 1, wherein the second container comprises a first port in fluid communication with the first port of the first container and a second port in fluid communication with the vacuum source whereby when the first container is substantially full with surgical fluid, the surgical fluid flows via the first port of the first container and through the first port of the second container.

9. A collector as claimed in claim 8, wherein the function of the first and second port of each container is interchangeable.

10. A collector as claimed in claim 8, wherein 3 or more containers are coupled in series, and have a combined capacity of at least 20 liters of surgical fluid.

11. A collector as claimed in claim 1, wherein the first port and the second port are coupled to the interior of the liner through first and second tubular bodies, and wherein the receptacle seals around the tubular bodies so that the container is adapted to collect surgical fluid in the liner when the tubular bodies are the only open passages through the receptacle.

12. A surgical fluid collection system comprising:

a plurality of containers, each container comprising:

a rigid receptacle which defines a vacuum chamber;

a liner disposable within the vacuum chamber of the receptacle, the liner defining a liner interior;

a vacuum port in fluid communication with the interior of the liner through the receptacle; and a fluid inflow port in fluid communication with the interior of the liner through the receptacle;

a surgical fluid inflow tube coupleable to the inflow valve of a first container to drain surgical fluids from a patient body; and an inter-container tube for coupling the fluid port of a second container with the vacuum port of the first container so that the surgical fluids flow through the vacuum port of the first container through the fluid inflow port of the second container when the liner of the first container is substantially full and;

a valve disposed between the interior of the liner and the vacuum chamber surrounding the liner, the valve allowing flow into the interior of the liner and preventing surgical fluid from flowing from the interior of the liner to the surrounding vacuum chamber.

13. A system as claimed in claim 12, wherein each liner holds at least 5 liters of surgical fluid, and wherein the liners have a combined capacity of at least 10 liters of surgical fluid.

14. A disposable surgical fluid collector liner for use with a rigid receptacle which defines a vacuum chamber, the receptacle having first and second passages into the vacuum chamber, the liner comprising:

a flexible pouch bordering an interior of the liner;

a vacuum port in fluid communication with the interior of the liner through the first passage of the receptacle;

a fluid inflow port in fluid communication with the interior of the liner through the second passage of the receptacle; and a valve disposable between the interior of the liner and the vacuum chamber surrounding the liner, the valve allowing flow into the interior of the liner and preventing surgical fluid from flowing from the interior of the liner to the surrounding vacuum chamber.

* * * * *